(12) United States Patent
Lucas

(10) Patent No.: US 6,362,388 B1
(45) Date of Patent: Mar. 26, 2002

(54) ADHESIVE BANDAGE

(76) Inventor: Gregory J. Lucas, Box 6651, Santa Rosa, CA (US) 95406

( * ) Notice: Subject to any disclaimer, the term of this patent is extended or adjusted under 35 U.S.C. 154(b) by 0 days.

(21) Appl. No.: 09/451,415

(22) Filed: Nov. 30, 1999

(51) Int. Cl.⁷ .................................................. A61F 13/00
(52) U.S. Cl. ............................. 602/57; 602/41; 602/43; 602/54; 602/56
(58) Field of Search ................................ 602/41–59, 74; 128/888, 889; D24/189; 206/440, 441

(56) References Cited

U.S. PATENT DOCUMENTS

| | | |
|---|---|---|
| 1,643,926 A | 9/1927 | Dickson |
| 2,005,676 A | 6/1935 | Hanover |
| 2,068,703 A * | 1/1937 | Powdermaker .............. 602/57 |
| 2,133,609 A | 10/1938 | Eustis |
| 2,353,332 A | 7/1944 | Hall |
| 2,469,064 A | 5/1949 | Campbell |
| 2,473,062 A | 6/1949 | Kennedy et al. |
| 3,085,024 A | 4/1963 | Blackford |
| 4,393,150 A | 7/1983 | Kresner |
| 4,427,737 A | 1/1984 | Cilento et al. |
| 4,530,353 A | 7/1985 | Lauritzen |
| 4,773,409 A | 9/1988 | Cilento et al. |
| 4,930,500 A | 6/1990 | Morgan |
| 5,213,565 A | 5/1993 | Rollband |
| 5,275,284 A * | 1/1994 | Onotsky ..................... 206/441 |
| 5,330,814 A | 7/1994 | Fewell |
| 5,480,377 A | 1/1996 | Cartmell et al. |
| 5,709,651 A * | 1/1998 | Ward ........................... 602/57 |
| 5,843,011 A | 12/1998 | Lucas |

* cited by examiner

Primary Examiner—Kim M. Lewis
(74) Attorney, Agent, or Firm—George W. Wasson; Mark Blumenkrantz

(57) ABSTRACT

An adhesive bandage includes a carrier strip having at least one adhesive portion and a dressing element disposed adjacent to the adhesive portion(s) along the entire length of the carrier strip. The width of the carrier strip is greater than the width of the dressing element.

1 Claim, 7 Drawing Sheets

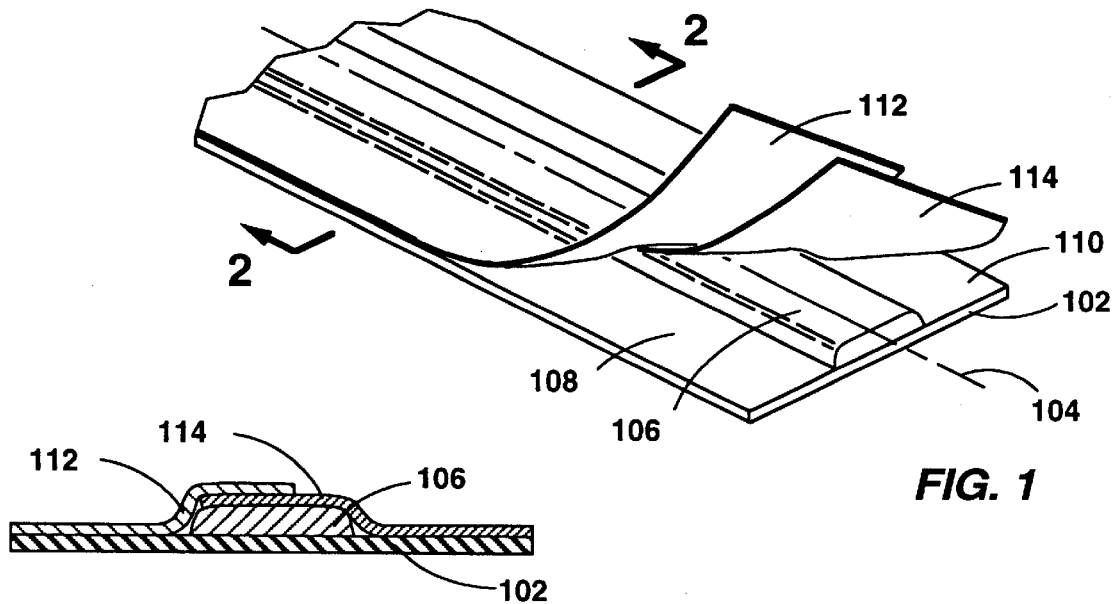
FIG. 1
FIG. 2
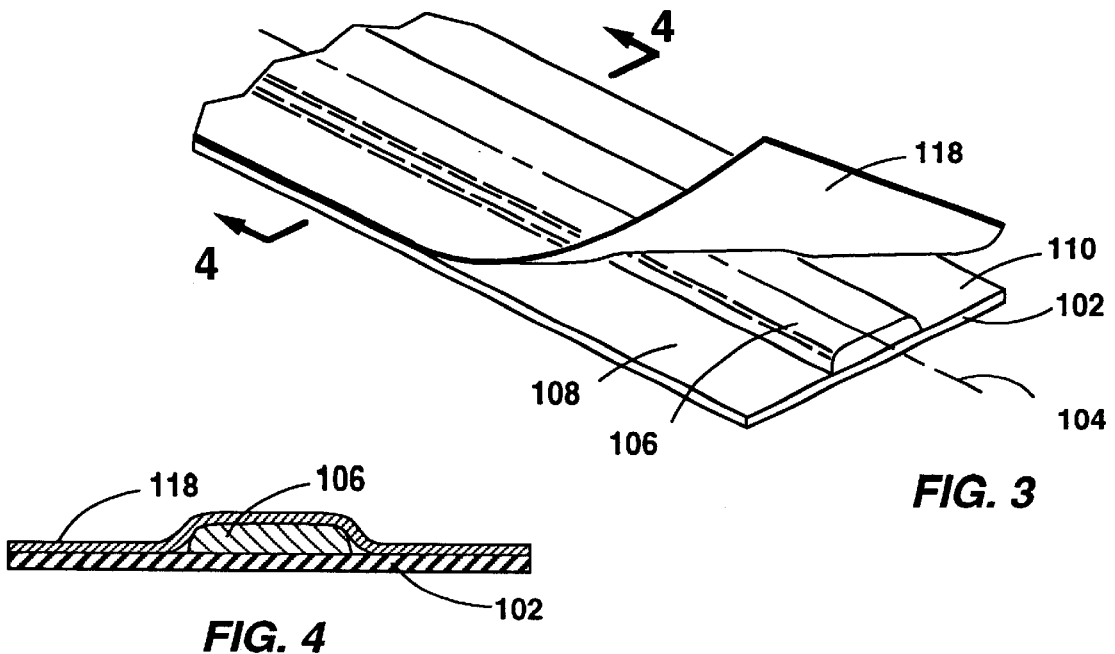
FIG. 3
FIG. 4

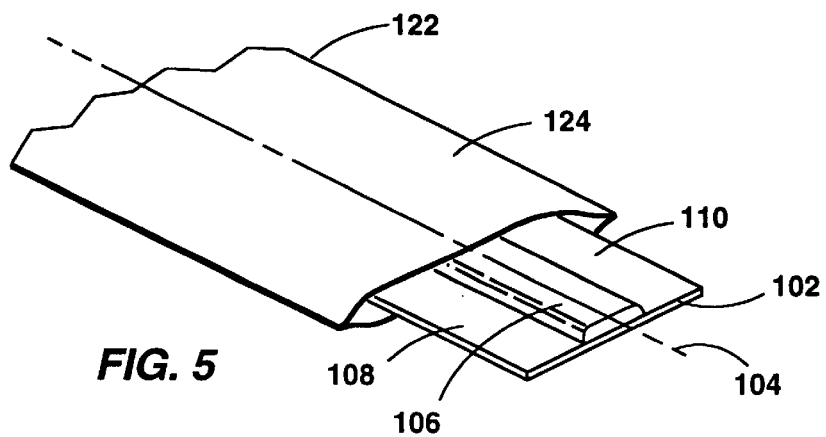
FIG. 5
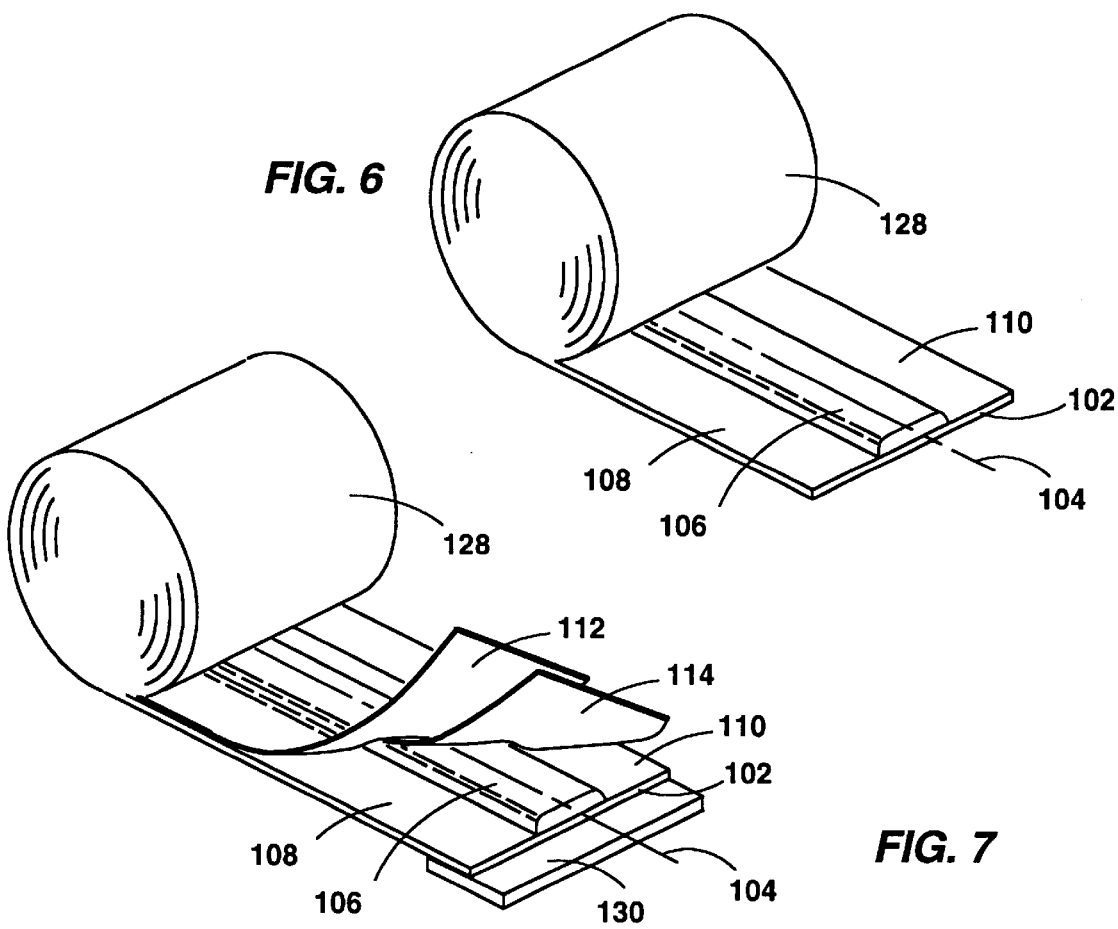
FIG. 6
FIG. 7

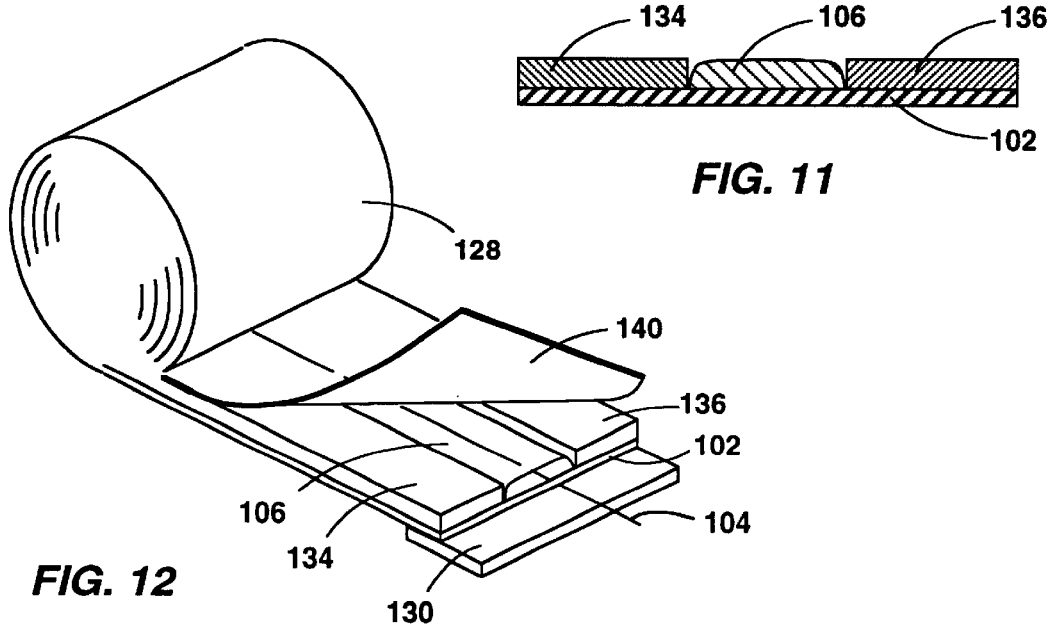
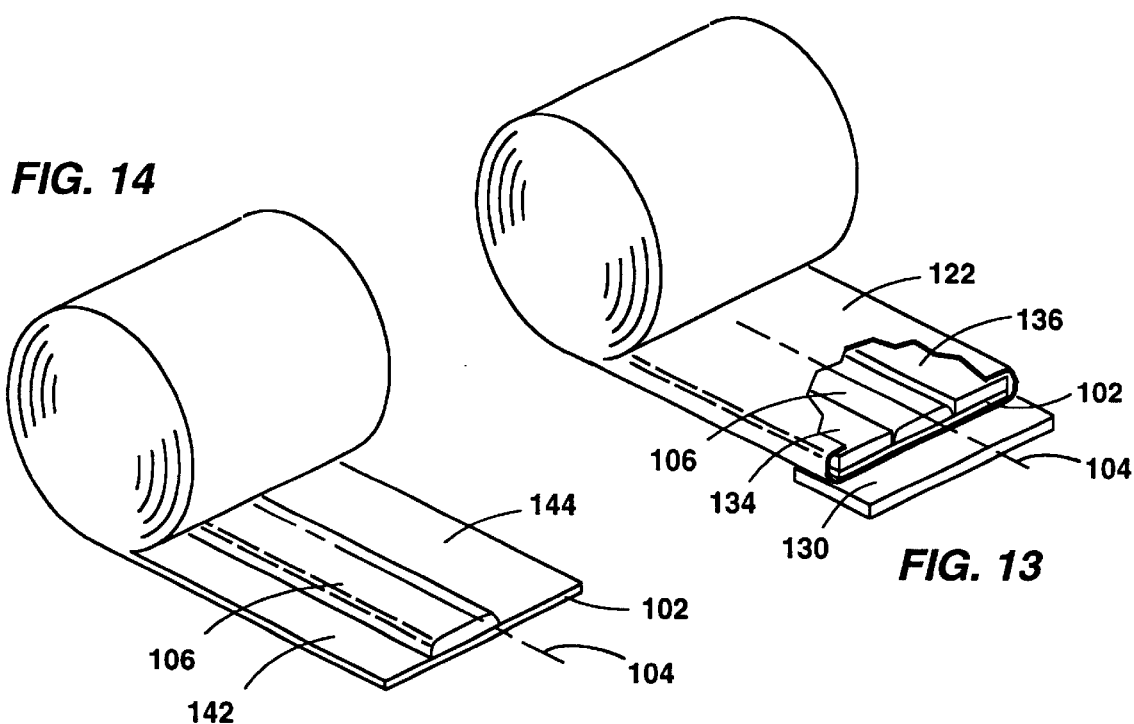

ADHESIVE BANDAGE

CROSS-REFERENCE TO RELATED APPLICATIONS

Not applicable.

STATEMENT REGARDING FEDERALLY-SPONSORED RESEARCH OR DEVELOPMENT

Not applicable.

REFERENCE TO MICROFICHE APPENDIX

Not applicable

BACKGROUND OF THE INVENTION

This invention relates to bandages, particularly to adhesive wound dressings.

A wound dressing comprising a carrier (backing) strip with adhesive areas for attachment to dry body surfaces is well-known in the art. A bandage of this type generally includes a pad made of an absorbent material to be positioned over the wound. The pad is secured to the carrier strip such that the pad occupies only a portion of the strip in the longitudinal direction of the strip. Even though bandages of this design work well for small wounds and abrasions, they are not optimally suited for treating elongated wounds because of the limited area of coverage offered by the absorbent pad. To dress an elongated wound, several bandages of the above-described construction must be applied side-by-side, transversely to the wound. Treating the wound in such a manner is time-consuming, inefficient, and unnecessarily conspicuous. Furthermore, an elongated wound may be located such that the application of several conventional bandages arranged side-by-side is impractical, e.g., next to the patient's hairline, mouth, or eye.

Hence, a need arises for an adhesive wound dressing that enables treatment of elongated wounds, that can be applied quickly, that is inconspicuous, and that can be used on areas of the body where application of conventional bandages is impractical.

SUMMARY OF THE INVENTION

An adhesive bandage is disclosed. The bandage comprises a carrier strip having at least one adhesive portion. The bandage also includes a dressing element disposed along the entire length of the carrier strip adjacent to the adhesive portion(s). The width of the carrier strip exceeds that of the dressing element.

The advantages of the invention will become apparent after consideration of the ensuing description and the accompanying drawings.

BRIEF DESCRIPTION OF THE DRAWINGS

The present invention is illustrated by way of example, and not by way of limitation, in the figures of the accompanying drawings, where:

FIG. 1 is a perspective view of an adhesive bandage with a centrally-located ribbon-like dressing element and dual protective sheets.

FIG. 2 is a sectional view taken along the lines 2—2 of FIG. 1.

FIG. 3 is a perspective view of an adhesive bandage with a centrally-located ribbon-like dressing element and a single protective sheet.

FIG. 4 is a sectional view taken along the lines 4—4 of FIG. 3.

FIG. 5 is a perspective view of an adhesive bandage with a centrally-located ribbon-like dressing element and a protective jacket.

FIG. 6 is a perspective view of a convolute adhesive bandage with a centrally-located ribbon-like dressing element.

FIG. 7 is a perspective view of the adhesive bandage of FIG. 1 in convolute form.

FIG. 11 is a sectional view taken along the lines 11—11 of FIG. 10.

FIG. 12 is a perspective view of a convolute adhesive bandage having a centrally-located ribbon-like dressing element, a pair of foundation sheets, and a single protective sheet.

FIG. 13 is a perspective view of a convolute adhesive bandage having a centrally-located ribbon-like dressing element, a pair of foundation sheets, and a protective jacket.

FIG. 14 is a perspective view of a convolute adhesive bandage having an offset ribbon-like dressing element.

For purposes of illustration, these figures are not necessarily drawn to scale. In all of the figures, like components are designated by like reference numerals.

DETAILED DESCRIPTION OF THE INVENTION

Figure 8:
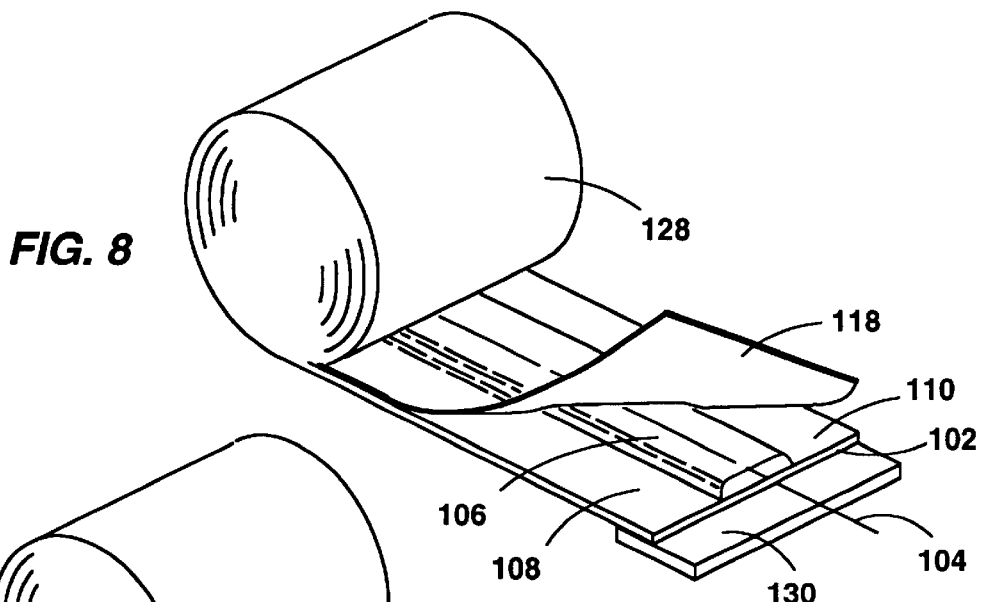
FIG. 8 is a perspective view of the adhesive bandage of FIG. 3 in convolute form.

Throughout the following description, specific details are set forth in order to provide a more thorough understanding of the invention. However, the invention may be practiced without these particulars. In other instances, well known elements have not been shown or described to avoid unnecessarily obscuring the invention. Accordingly, the specification and drawings are to be regarded in an illustrative, rather than a restrictive, sense.

FIG. 1 is a perspective view of an adhesive bandage according to one embodiment of the invention. The adhesive bandage comprises a carrier strip 102 having a longitudinal symmetry axis 104. A ribbon-like dressing element 106 is centrally disposed along the entire length of carrier strip 102. Carrier strip 102 further includes adhesive portions 108 and 110, located adjacent to dressing element 106. Protective sheets 1 12 and 114 are releasably attached to adhesive portions 108 and 110, respectively. The protective sheets overlap, thereby shielding dressing element 106 from the environment. A sectional view of the adhesive bandage taken along the lines 2—2 of FIG. 1 is illustrated in FIG. 2. As apparent from FIG. 2, the thickness of dressing element 106 is greater than that of individual protective sheets 112 and 114. The adhesive bandage according to this embodiment of the invention may be manufactured in strips of various predetermined lengths and in a convolute form.

FIG. 3 is a perspective view of a variation of the adhesive bandage shown in FIG. 1. The adhesive bandage of FIG. 3 includes a single protective sheet 118, releasably attached to adhesive portions 108 and 110 and providing a shield for dressing element 106. A sectional view of the adhesive bandage taken along the lines 4—4 of FIG. 3 is illustrated in FIG. 4. As apparent from FIG. 4, the thickness of dressing element 106 is greater than that of protective sheet 118. The adhesive bandage of this configuration may be manufactured in strips of various predetermined lengths or in a convolute form.

FIG. 5 is a perspective view of the adhesive bandage according to yet another embodiment of the invention. The adhesive bandage illustrated in FIG. 5 includes a protective jacket 122, wherein carrier strip 102 is encased. To access strip 102, jacket 122 must be cut or torn open and a top portion 124 of the jacket, releasably adhering to adhesive portions 108 and 110, must be pealed away. The bandage according to this embodiment of the invention may be manufactured in a convolute form or in strips of various predetermined lengths.

Figure 9:
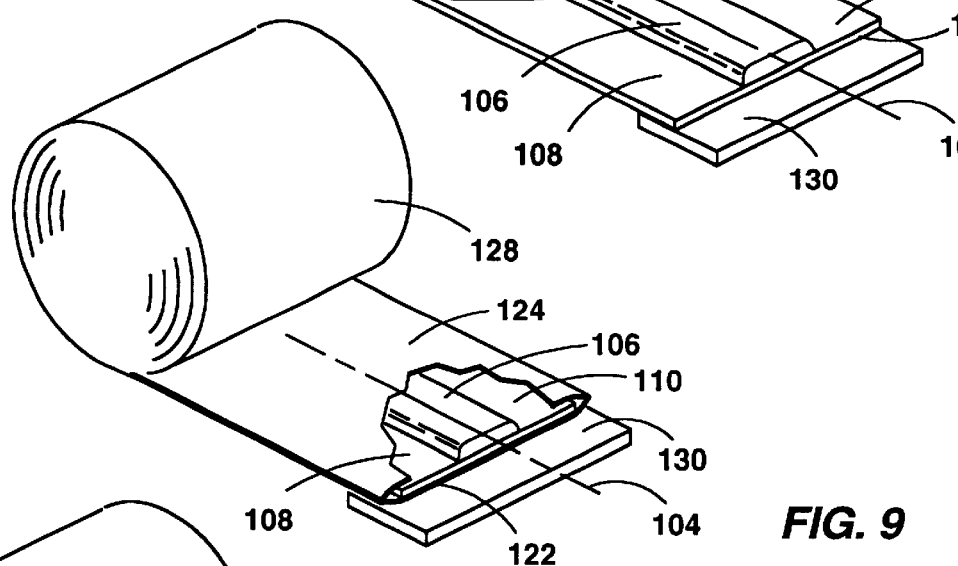
FIG. 9 is a perspective view of the adhesive bandage of FIG. 5 in convolute form.

FIG. 6 shows an embodiment where the adhesive bandage is wound in a roll, with adhesive portions 108 and 110 releasably adhering to the back side 128 of carrier strip 102 to prevent the bandage from uncoiling. In like manner, FIGS. 7, 8, and 9, illustrate adhesive bandages of FIGS. 1, 3, and 5, respectively, packaged in convolute form. As shown in FIGS. 7 and 8, a segment of adhesive material 130 may be releasably attached to the back side of strip 102 at the end of the roll. To prevent the roll from uncoiling, the exposed adhesive surface of segment 130 should be releasably secured to back side 128 of the carrier strip forming the roll. In FIG. 9, segment 130 is shown attached to the back side of protective jacket 122 to provide the same function.

Figure 10:
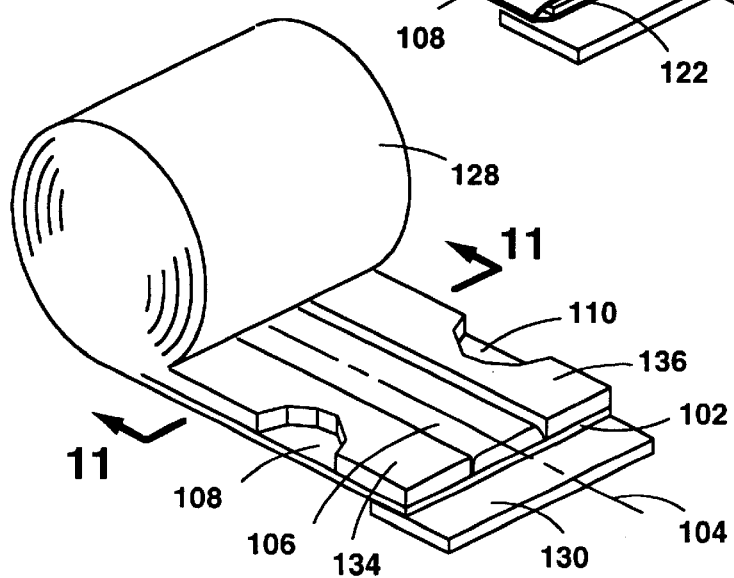
FIG. 10 is a perspective view of a convolute adhesive bandage having a centrally-located ribbon-like dressing element and a pair of foundation sheets.

To facilitate rolling the adhesive bandage into a spiral and to aid in maintaining the lateral stability of the resulting bandage roll, in yet another embodiment of the invention the adhesive bandage is provided with foundation sheets 134 and 136 (FIG. 10), releasably attached to adhesive portions 108 and 110, respectively. As evident from FIG. 11, the thickness of each foundation sheet is substantially the same as the thickness of dressing element 106. To prevent the bandage roll from uncoiling, releasably-adhesive segment 130 may be provided on the back side of strip 102 at the end of the roll, as shown in FIG. 10. Alternatively, the top faces of foundation sheets 134 and 136 may be coated with adhesive for releasably adhering to back side 128 of the carrier strip forming the roll.

In another embodiment of the invention, shown in FIG. 12, the adhesive bandage includes a protective sheet 140 releasably adhering to foundation sheets 134 and 136. In this configuration, the top faces of foundation sheets 134 and 136 are coated with adhesive. To prevent the bandage roll from uncoiling, releasably-adhesive segment 130 may be provided on the back side of strip 102 at the end of the roll. Alternatively, the top face of protective sheet 140 may be coated with adhesive for releasably adhering to back side 128 of the carrier strip forming the roll.

As shown in FIG. 13, a convolute adhesive bandage having foundation sheets 134 and 136 may be also manufactured encased in a protective jacket 122. To prevent the bandage roll from uncoiling, releasably-adhesive segment 130 may be provided on the back side of jacket 122 at the end of the roll.

Figure 15:
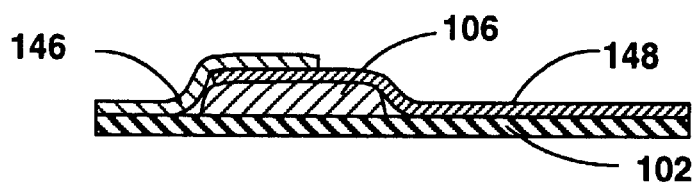
FIG. 15 is a sectional view of an adhesive bandage having an offset ribbon-like dressing element and a pair of protective sheets.
Figure 16:
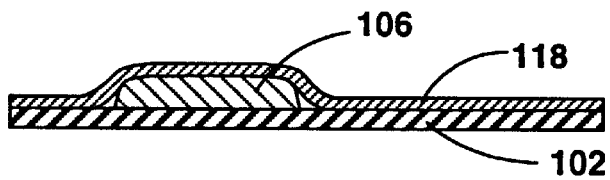
FIG. 16 is a sectional view of an adhesive bandage having an offset ribbon-like dressing element and a single protective sheet.
Figure 17:
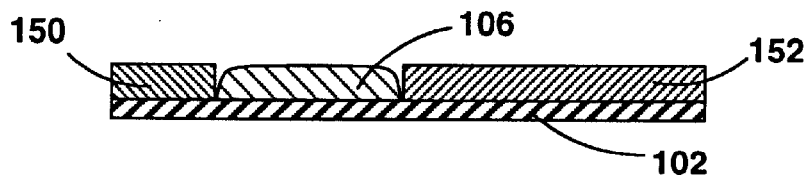
FIG. 17 is a sectional view of an adhesive bandage having an offset ribbon-like dressing element and a pair of foundation sheets.
Figure 18:
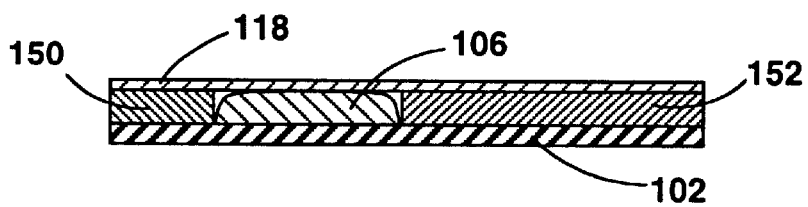
FIG. 18 is a sectional view of an adhesive bandage having an offset ribbon-like dressing element, a pair of foundation sheets, and a single protective sheet.
Figure 19:
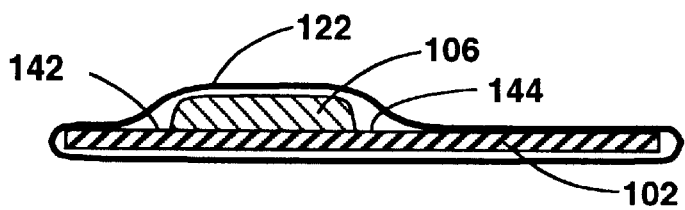
FIG. 19 is a sectional view of an adhesive bandage having an offset ribbon-like dressing element and a protective jacket.

FIG. 14 illustrates an embodiment of the adhesive bandage where ribbon-like dressing element 106, disposed along the entire length of carrier strip 102, is offset from longitudinal symmetry axis 104. Carrier strip 102 includes adhesive portions 142 and 144 of unequal width. Variations of the adhesive bandage with offset dressing element 106 are shown in FIGS. 15–19. FIG. 15 shows an adhesive bandage with two protective sheets 146 and 148. FIG. 16 illustrates a bandage with a single protective sheet 118. A bandage having foundation sheets 150 and 152 is pictured in FIG. 17. FIG. 18 shows a bandage with foundation sheets 150, 152 and a single protective sheet 118. FIG. 19 illustrates the bandage of FIG. 14 encased in a protective jacket 122, which may also be used with adhesive bandages of FIGS. 15–18.

Figure 20:
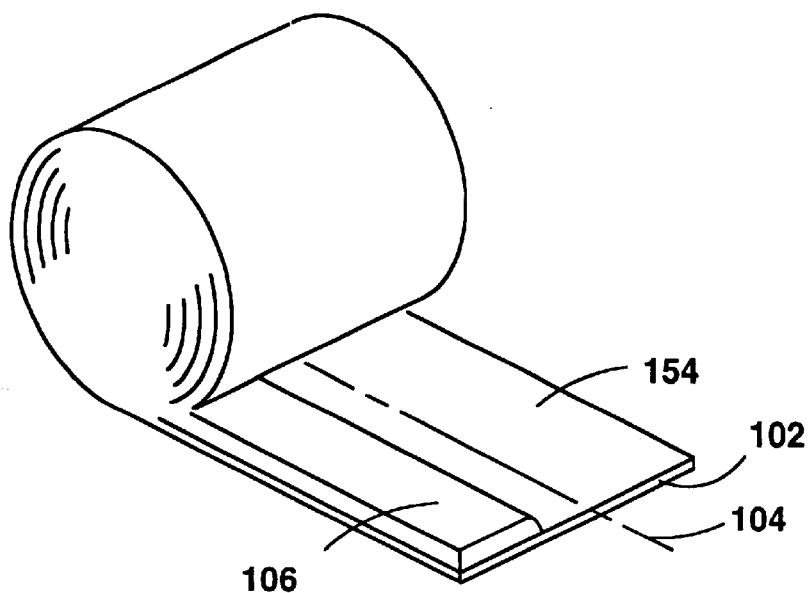
FIG. 20 is a perspective view of a convolute adhesive bandage having a ribbon-like dressing element disposed along the edge of the carrier strip.
Figure 21:
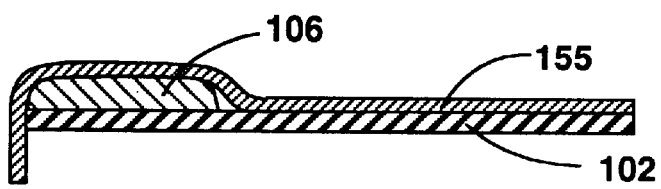
FIG. 21 is a sectional view of an adhesive bandage having a single protective sheet and a ribbon-like dressing element disposed along the edge of the carrier strip.
Figure 22:
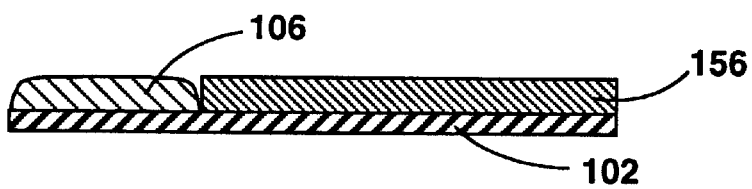
FIG. 22 is a sectional view of an adhesive bandage having a single foundation sheet and a ribbon-like dressing element disposed along the edge of the carrier strip.
Figure 23:
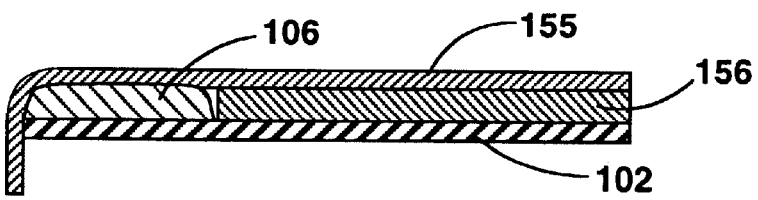
FIG. 23 is a sectional view of an adhesive bandage having a single foundation sheet, a single protective sheet, and a ribbon-like dressing element disposed along the edge of the carrier strip.
Figure 24:
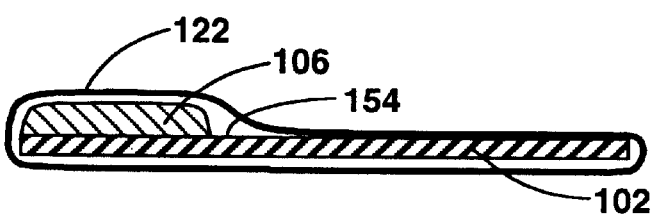
FIG. 24 is a sectional view of an adhesive bandage having a protective jacket and a ribbon-like dressing element disposed along the edge of the carrier strip.

Other embodiments of the adhesive bandage are discussed with reference to FIGS. 20–24. FIG. 20 illustrates an adhesive bandage with a ribbon-like dressing element 106 longitudinally disposed along the entire length of carrier strip 102 at one edge thereof. Carrier strip 102 further includes an adhesive portion 154 located adjacent to dressing element 106. FIG. 21 shows an adhesive bandage of FIG. 20 further including a protective sheet 155. A bandage having a foundation sheet 156 is pictured in FIG. 22. FIG. 23 shows a bandage with foundation sheet 156 and protective sheet 155. FIG. 24 illustrates the bandage of FIG. 20 encased in a protective jacket 122, which may also be used with adhesive bandages of FIGS. 21–24.

Figure 25:
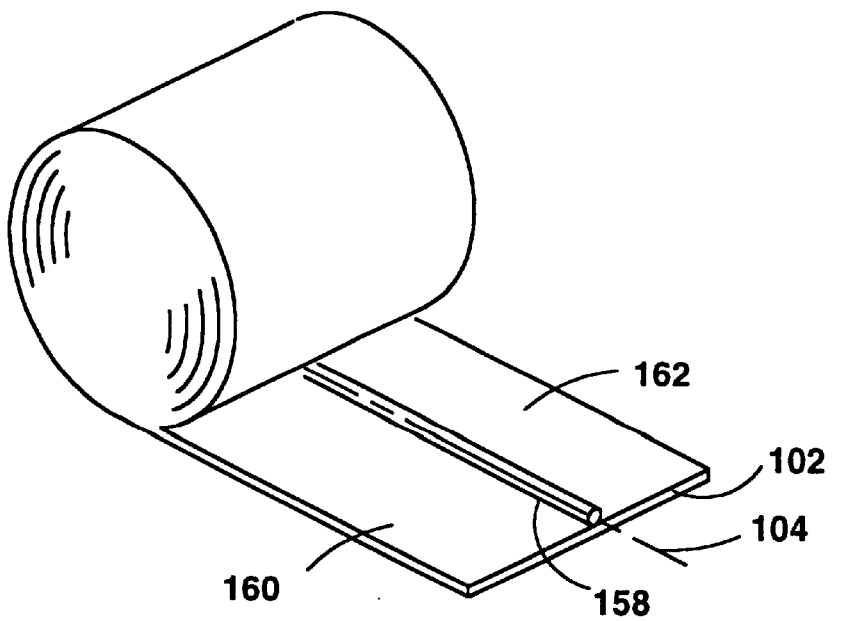
FIG. 25 is a perspective view of a convolute adhesive bandage having a thread-like dressing element centrally-disposed along the carrier strip.
Figure 26:
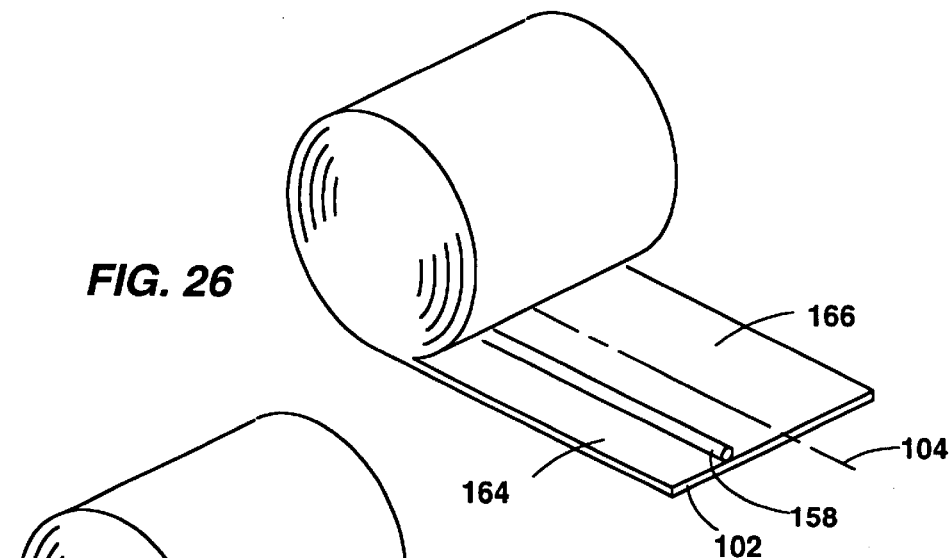
FIG. 26 is a perspective view of a convolute adhesive bandage having a thread-like dressing element offset from the central axis of the carrier strip.
Figure 27:
FIG. 27 is a perspective view of a convolute adhesive bandage having a thread-like dressing element disposed along the edge of the carrier strip.

Still other embodiments of the adhesive bandage are discussed with reference to FIGS. 25–27. FIG. 25 illustrates an adhesive bandage having a thread-like dressing element 158 disposed centrally along the entire length of carrier strip 102. The carrier strip includes adhesive portions 160 and 162, adjacent to dressing element 158. An adhesive bandage with thread-like dressing element 158, disposed along the entire length of carrier strip 102 and offset from symmetry axis 104, is shown in FIG. 26. In this embodiment of the invention, carrier strip 102 includes adhesive portions 164 and 166, having different widths and located adjacent to dressing element 158. Additionally, FIG. 27 shows an adhesive bandage where thread-like dressing element 158 is disposed along the entire length of carrier strip 102 at one edge thereof. Element 158 is adjacent to adhesive portion 168. Furthermore, the various embodiments of the invention shown in FIGS. 1–24 can be modified to replace ribbon-like dressing element 106 with thread-like dressing element 158. Accordingly, such embodiments of the invention can be contemplated with reference to the above-identified drawing figures.

Figure 28:
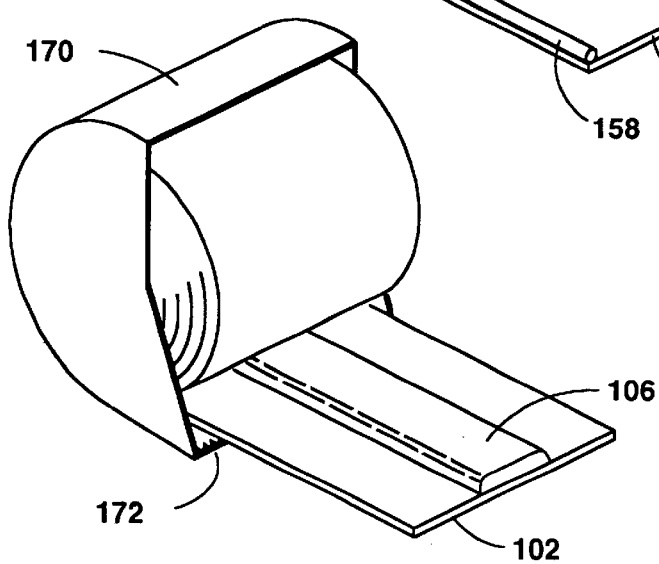
FIG. 28 is a perspective view of a convolute adhesive bandage provided in a dispenser.

For added convenience, the adhesive bandage in convolute form as described in the embodiments above may be coupled with a known manually-operated dispenser 170, generally represented in FIG. 28. The dispenser may include a cutting edge 172 for severing the adhesive bandage, or may simply be a spool on which the adhesive bandage is wound. In the latter case, adhesive bandage strips of the required length may be severed from the bandage roll using a sharp instrument, e.g., scissors.

Depending on the required application, the dressing element of the adhesive bandage may be made of various materials. For instance, it is well-known in the art to manufacture the dressing element out of gauze and cotton fibers or similar materials and bond the dressing element to the carrier strip, e.g., with a pressure-sensitive adhesive. The dressing element may be medicated if required. Alternatively, the dressing element may be an air-permeable, hydrophilic gel material deposited onto the carrier strip, as disclosed in, e.g., U.S. Pat. No. 4,930,500 to Morgan. A hydrogel material of the type disclosed in U.S. Pat. No. 5,480,377 to Cartmell et al. may also be used to manufacture the dressing element in accordance with the various embodiment of the invention. If absorption of the wound exudate is of primary importance, the dressing element may be manufactured in the form of closed cell polyurethane foam, as taught, for example, in U.S. Pat. No. 4,773,409 to Cilento et al. Many other variants of the dressing-element composition are well known in the art and may be substituted as required.

Similarly, the carrier strip of the adhesive bandage disclosed in the embodiments above may be manufactured in any of a number of different ways well known to one of ordinary skill in the art. For example, the carrier strip may comprise breathable tape with microporous adhesive, such as disclosed in U.S. Pat. No. 4,427,737 to Cilento et al. Alternatively, the carrier strip may be made of known non-breathable or even hydrophobic woven and non-woven materials.

The physical dimensions of the adhesive bandage disclosed in the various embodiments of the invention may vary according to the required application. For example, the bandage may be used for treating wounds resulting from surgical incisions in the chest cavity or in other parts of the human anatomy. The dimensions of the carrier strip and the dressing element would be sized in accordance with the particular application. Generally, deeper or more jagged wounds require a carrier strip having a greater width for positive adhesion to the areas around the wound and a bulkier dressing element for maximum coverage and absorption of wound exudate. For instance, a heavy-duty adhesive bandage would be needed for veterinary use in the treatment of large animals. For heavy-duty and general-purpose use, the adhesive bandage having a ribbon-like dressing element (FIGS. 1–24) is generally utilized. On the other hand, the adhesive bandage having a thread-like dressing element (FIGS. 25–27) may be useful for treating shallower or cleanly-formed wounds, such as those resulting from precise incisions performed during cosmetic surgery.

Where the area available for the adhesion of the bandage on one side of the wound is greater than the area on the other side, the adhesive bandage having a dressing element offset from the longitudinal axis of the carrier strip may be utilized (FIGS. 14 and 26). Similarly, if no room is available for adhesion on one side of the wound, e.g., when the wound is located along the hairline on the forehead of a patient, the adhesive bandage with the dressing element disposed along the edge of the carrier strip (FIGS. 20 and 27) is most useful.

To utilize the bandage as disclosed in the various embodiments of the invention, the existing combination of protective sheets, foundation sheets, and/or protective jacket must be removed from the carrier strip after the required length of bandage has been severed. The dressing element should be placed over the wound and light pressure applied to the back side of the carrier strip to help adhere the bandage to the area(s) near the wound.

Many other modifications of the adhesive bandage as disclosed in the various embodiments of the invention are possible. The above configurations of the adhesive bandage are given only as examples. Therefore, the scope of the invention should be determined not by the illustrations given, but by the appended claims and their equivalents.

What is claimed is:

1. A bandage including:

a carrier strip having at least one adhesive portion;

a dressing element disposed along the entire length of said carrier strip adjacent to said at least one adhesive portion, the width of said carrier strip exceeding the width of said dressing element;

at least one foundation sheet releasably attached to only said at least one adhesive portion, said at least one foundation sheet having substantially, the same thickness as the dressing elements; and at least one protective sheet releasably attached to said at least one foundation sheet.

\* \* \* \* \*